United States Patent
Datta et al.

(10) Patent No.: US 6,569,139 B1
(45) Date of Patent: May 27, 2003

(54) DISPOSABLE ABSORBENT UNDERPANTS FOR CONTAINING BODY FLUID

(75) Inventors: Paul Joseph Datta, Appleton, WI (US); Michael Barth Venturino, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 320 days.

(21) Appl. No.: 09/599,757

(22) Filed: Jun. 22, 2000

(51) Int. Cl.⁷ ................................................ A61F 13/15
(52) U.S. Cl. .............................. 604/385.27; 604/385.24
(58) Field of Search ...................... 604/385.24, 385.27, 604/385.28, 385.01

(56) References Cited

U.S. PATENT DOCUMENTS

| | | | | |
|---|---|---|---|---|
| 2,119,610 A | 6/1938 | Tasker | ................ | 128/284 |
| 2,125,495 A | 8/1938 | French | ................ | 154/2 |

(List continued on next page.)

FOREIGN PATENT DOCUMENTS

| | | | | |
|---|---|---|---|---|
| CA | 2 040 578 | 10/1991 | ............ | A61F/13/15 |
| EP | 0 048 011 A1 | 3/1982 | ............ | A41B/13/02 |
| EP | 0 412 579 B1 | 2/1991 | ............ | A61F/13/15 |
| EP | 0 456 885 A1 | 11/1991 | ............ | A61F/13/15 |
| EP | 0 241 925 B1 | 9/1992 | ............ | A61F/13/66 |
| EP | 0 531 666 A1 | 3/1993 | ............ | B29C/65/08 |
| EP | 0 539 703 A1 | 5/1993 | ............ | A61F/13/15 |
| EP | 0 623 331 B1 | 11/1994 | ............ | A61F/13/15 |
| EP | 0 627 210 A3 | 12/1994 | ............ | A61F/13/15 |
| EP | 0 483 692 B1 | 6/1995 | ............ | A61F/13/15 |
| EP | 0 487 921 B1 | 9/1995 | ............ | A61F/13/15 |
| EP | 0 452 951 B1 | 11/1995 | ............ | A61F/13/15 |
| EP | 0 753 292 A2 | 1/1997 | ............ | A61F/13/15 |
| EP | 0 832 629 A2 | 4/1998 | ............ | A61F/13/15 |
| EP | 1 027 874 A2 | 8/2000 | ......... | A61F/13/496 |
| GB | 2 176 962 A | 1/1987 | ............ | A41B/9/00 |
| GB | 2 245 149 B | 1/1992 | ............ | A61F/13/15 |
| GB | 2 253 131 B | 9/1992 | ............ | A61F/13/72 |
| GB | 2 257 652 A | 1/1993 | ............ | B29C/65/08 |
| JP | 57-77304 A | 5/1982 | ............ | A41B/13/02 |
| JP | 3-139349 | 6/1991 | ............ | A61F/13/54 |
| JP | 4-161152 | 6/1992 | ............ | A61F/13/15 |
| JP | 4-364845 A | 12/1992 | ............ | A61F/13/54 |
| WO | WO 93/17648 A1 | 9/1993 | ............ | A61F/13/15 |
| WO | WO 95/06451 A1 | 3/1995 | ............ | A61F/13/15 |
| WO | WO 96/23468 A1 | 8/1996 | ............ | A61F/13/15 |
| WO | WO 96/40035 A1 | 12/1996 | ............ | A61F/13/72 |
| WO | WO 99/25296 A1 | 5/1999 | ............ | A61F/13/15 |
| WO | WO 00/02511 A1 | 1/2000 | ............ | A61F/13/15 |

OTHER PUBLICATIONS

Derwent World Patent Database abstract of JP 58–11507 A: Description of Mitsubishi Chem. Ind. Ltd. (MITU), "Modified Polyethylene Resin With Good Adhesive and Mechanical Strength."

American Society for Testing Materials (ASTM) Designation: D 2495–87, "Standard Test Method For Moisture in Cotton by Oven–Drying," pp. 617–622, published Sep. 1987.

American Society for Testing Materials (ASTM) Designation: E 96–92, "Standard Test Methods for Water Vapor Transmission of Materials," pp. 702–709, published Mar. 1992.

* cited by examiner

*Primary Examiner*—Weilun Lo
*Assistant Examiner*—Michael Bogart
(74) *Attorney, Agent, or Firm*—Thomas J. Connelly; Scott A. Baum (57) ABSTRACT

A disposable absorbent underpants for containing body fluid includes a first pair of leg elastics, a second pair of leg elastics, and a third pair of leg elastics. Each of the third pair of leg elastics is a distinct member containing at least one strand of elastic that is partially enclosed by a carrier sheet. Each of the third pair of leg elastics is separated from at least one of the first or the second pair of leg elastics by a gap.

23 Claims, 4 Drawing Sheets

U.S. PATENT DOCUMENTS

| | | | |
|---|---|---|---|
| 2,408,723 A | 10/1946 | Arpin et al. | 2/224 |
| 2,733,715 A | 2/1956 | Folk | 128/284 |
| 2,866,459 A | 12/1958 | Sobelson | 128/284 |
| 3,371,668 A | 3/1968 | Johnson | 128/290 |
| 3,468,748 A | 9/1969 | Bassett | 161/122 |
| 3,488,778 A | 1/1970 | Goujon et al. | 2/224 |
| 3,575,782 A | 4/1971 | Hansen | 161/141 |
| 3,599,640 A | 8/1971 | Larson | 128/286 |
| 3,912,565 A | 10/1975 | Koch et al. | 156/85 |
| 3,985,003 A | 10/1976 | Reed | 66/196 |
| 4,022,212 A | 5/1977 | Lovison | 128/288 |
| 4,081,301 A | 3/1978 | Buell | 156/164 |
| 4,093,204 A | 6/1978 | Landgraf et al. | 270/21 |
| 4,196,245 A | 4/1980 | Kitson et al. | 428/198 |
| 4,205,679 A | 6/1980 | Repke et al. | 128/287 |
| 4,210,143 A | 7/1980 | De Jonckheere | 128/287 |
| 4,227,531 A | 10/1980 | McLeod | 128/288 |
| 4,227,952 A | 10/1980 | Sabee | 156/164 |
| 4,236,257 A | 12/1980 | Williams et al. | 2/406 |
| 4,240,866 A | 12/1980 | Rega | 156/496 |
| 4,241,462 A | 12/1980 | Tagawa et al. | 2/406 |
| 4,244,059 A | 1/1981 | Pflaumer | 2/400 |
| 4,244,367 A | 1/1981 | Rollenhagen | 128/288 |
| 4,253,461 A | 3/1981 | Strickland et al. | 128/287 |
| 4,269,188 A | 5/1981 | Nishizawa et al. | 128/287 |
| 4,285,342 A | 8/1981 | Mesek | 128/287 |
| 4,297,157 A | 10/1981 | Van Vliet | 156/164 |
| 4,300,241 A | 11/1981 | Shaull | 2/400 |
| 4,300,562 A | 11/1981 | Pieniak | 128/287 |
| 4,300,967 A | 11/1981 | Sigl | 156/164 |
| 4,302,853 A | 12/1981 | Mesek | 2/402 |
| 4,304,021 A | 12/1981 | Theodorsen | 12/142 R |
| 4,323,070 A | 4/1982 | Ternstrom et al. | 128/287 |
| 4,325,372 A | 4/1982 | Teed | 128/289 |
| 4,327,448 A | 5/1982 | Lunt | 2/404 |
| 4,338,939 A | 7/1982 | Daville | 128/286 |
| 4,344,999 A | 8/1982 | Gohlke | 428/212 |
| 4,351,340 A | 9/1982 | McLeod | 128/288 |
| D266,591 S | 10/1982 | Ryan | D24/50 |
| 4,352,355 A | 10/1982 | Mesek et al. | 128/287 |
| 4,352,356 A | 10/1982 | Tong | 128/288 |
| 4,355,425 A | 10/1982 | Jones et al. | 2/402 |
| 4,385,224 A | 5/1983 | Kaufman et al. | 219/469 |
| 4,390,999 A | 7/1983 | Lawson et al. | 2/409 |
| 4,397,645 A | 8/1983 | Buell | 604/380 |
| 4,405,536 A | 9/1983 | Woodcock | 264/25 |
| 4,407,284 A | 10/1983 | Pieniak | 604/385 |
| 4,409,049 A | 10/1983 | Passafiume et al. | 156/164 |
| 4,411,660 A | 10/1983 | Dawn et al. | 604/396 |
| 4,412,881 A | 11/1983 | Sigl | 156/164 |
| 4,425,127 A | 1/1984 | Suzuki et al. | 604/366 |
| 4,425,128 A | 1/1984 | Motomura | 604/381 |
| 4,427,408 A | 1/1984 | Karami et al. | 604/393 |
| 4,430,086 A | 2/1984 | Repke | 604/385 |
| 4,432,823 A | 2/1984 | Moore | 156/164 |
| 4,450,026 A | 5/1984 | Pieniak et al. | 156/164 |
| 4,490,148 A | 12/1984 | Beckestrom | 604/385.2 |
| 4,498,944 A | 2/1985 | Krause et al. | 156/205 |
| 4,499,139 A | 2/1985 | Schortmann | 428/245 |
| 4,501,792 A | 2/1985 | Holmes et al. | 428/299 |
| RE31,922 E | 6/1985 | Mesek et al. | 604/385 A |
| 4,522,874 A | 6/1985 | Pommez | 428/284 |
| 4,534,769 A | 8/1985 | De Jonckheere et al. | 604/369 |
| 4,536,181 A | 8/1985 | Cook | 604/387 |
| 4,548,859 A | 10/1985 | Kline et al. | 428/251 |
| 4,552,795 A | 11/1985 | Hansen et al. | 428/110 |
| 4,555,244 A | 11/1985 | Buell | 604/392 |
| 4,555,245 A | 11/1985 | Armbruster | 604/396 |
| 4,555,811 A | 12/1985 | Shimalla | 2/51 |
| 4,560,381 A | 12/1985 | Southwell | 604/396 |
| 4,573,986 A | 3/1986 | Minetola et al. | 604/366 |
| 4,585,448 A | 4/1986 | Enloe | 604/378 |
| 4,586,199 A | 5/1986 | Birring | 2/401 |
| 4,597,110 A | 7/1986 | Smith, Sr. et al. | 2/408 |
| 4,601,717 A | 7/1986 | Blevins | 604/358 |
| 4,606,079 A | 8/1986 | DeWoskin | 2/338 |
| 4,610,680 A | 9/1986 | LaFleur | 604/385 A |
| 4,610,681 A | 9/1986 | Strohbeen et al. | 604/396 |
| 4,612,674 A | 9/1986 | Hashimoto | 2/406 |
| 4,615,051 A | 10/1986 | Hashimoto | 2/406 |
| 4,615,695 A | 10/1986 | Cooper | 604/385 A |
| 4,619,649 A | 10/1986 | Roberts | 604/396 |
| 4,626,305 A | 12/1986 | Suzuki et al. | 156/164 |
| 4,629,643 A | 12/1986 | Curro et al. | 428/131 |
| 4,636,207 A | 1/1987 | Buell | 604/370 |
| 4,639,949 A | 2/1987 | Ales et al. | 2/400 |
| 4,640,859 A | 2/1987 | Hansen et al. | 428/105 |
| 4,641,381 A | 2/1987 | Heran et al. | 2/400 |
| 4,642,818 A | 2/1987 | Dehnert et al. | 2/400 |
| 4,642,819 A | 2/1987 | Ales et al. | 2/400 |
| 4,646,362 A | 3/1987 | Heran et al. | 2/400 |
| 4,655,760 A | 4/1987 | Morman et al. | 604/385 A |
| 4,661,102 A | 4/1987 | Shikata et al. | 604/385 A |
| 4,664,663 A | 5/1987 | Brier | 604/387 |
| 4,666,542 A | 5/1987 | De Jonckheere | 156/164 |
| 4,671,793 A | 6/1987 | Hults et al. | 604/385 R |
| 4,674,135 A | 6/1987 | Greene | 2/400 |
| 4,675,016 A | 6/1987 | Meuli et al. | 604/385 A |
| 4,681,580 A | 7/1987 | Reising et al. | 604/385 A |
| 4,683,877 A | 8/1987 | Ersfeld et al. | 128/90 |
| 4,687,477 A | 8/1987 | Suzuki et al. | 604/385 A |
| 4,695,278 A | 9/1987 | Lawson | 604/385 A |
| 4,695,279 A | 9/1987 | Steer | 604/397 |
| 4,698,855 A | 10/1987 | Hicks | 2/402 |
| 4,699,823 A | 10/1987 | Kellenberger et al. | 428/419 |
| 4,718,902 A | 1/1988 | Bonito | 604/396 |
| 4,726,807 A | 2/1988 | Young et al. | 604/385 A |
| 4,729,131 A | 3/1988 | Thygesen | 2/400 |
| 4,735,622 A | 4/1988 | Acuff et al. | 604/361 |
| 4,736,468 A | 4/1988 | Efird et al. | 2/400 |
| 4,743,239 A | 5/1988 | Cole | 604/385 R |
| 4,743,241 A | 5/1988 | Igaue et al. | 604/385 A |
| 4,745,636 A | 5/1988 | Lunt | 2/402 |
| 4,756,942 A | 7/1988 | Aichele | 428/102 |
| 4,762,582 A | 8/1988 | de Jonckheere | 156/164 |
| 4,771,483 A | 9/1988 | Hooreman et al. | 2/237 |
| 4,795,451 A | 1/1989 | Buckley | 604/385.2 |
| 4,798,603 A | 1/1989 | Meyer et al. | 604/378 |
| 4,813,950 A | 3/1989 | Branch | 604/396 |
| 4,816,026 A | 3/1989 | Richardson | 604/385.2 |
| 4,838,886 A | 6/1989 | Kent | 604/392 |
| 4,842,666 A | 6/1989 | Werenicz | 156/161 |
| 4,880,420 A | 11/1989 | Pomparelli | 604/385.1 |
| 4,880,424 A | 11/1989 | Rautenberg | 604/396 |
| 4,883,480 A | 11/1989 | Huffman et al. | 604/385.1 |
| 4,883,481 A | 11/1989 | Blanchard | 604/385.1 |
| 4,898,594 A | 2/1990 | Cottenden | 604/397 |
| 4,909,804 A | 3/1990 | Douglas, Sr. | 604/385.2 |
| 4,928,323 A | 5/1990 | Nathan | 2/406 |
| 4,932,949 A | 6/1990 | Thygesen et al. | 604/386 |
| 4,932,950 A | 6/1990 | Johnson | 604/392 |
| 4,938,754 A | 7/1990 | Mesek | 604/385.2 |
| 4,940,463 A | 7/1990 | Leathers et al. | 604/396 |
| 4,940,464 A | 7/1990 | Van Gompel et al. | 604/396 |
| 4,950,264 A | 8/1990 | Osborn, III | 604/385.1 |
| 4,960,414 A | 10/1990 | Meyer | 604/395 |
| 4,977,011 A | 12/1990 | Smith | 428/152 |
| 4,984,584 A | 1/1991 | Hansen et al. | 128/898 |
| 4,992,125 A | 2/1991 | Suzuki et al. | 156/164 |
| 4,995,928 A | 2/1991 | Sabee | 156/164 |
| 5,019,067 A | 5/1991 | Simmons | 604/385.2 |

| Patent | Date | Inventor | Class |
|---|---|---|---|
| 5,024,667 A | 6/1991 | Malcolm et al. | 604/382 |
| 5,031,248 A | 7/1991 | Kemper | 2/406 |
| 5,037,417 A | 8/1991 | Ternstrom et al. | 609/385.2 |
| 5,055,103 A | 10/1991 | Nomura et al. | 604/385.2 |
| 5,057,571 A | 10/1991 | Malcolm et al. | 524/505 |
| 5,062,839 A | 11/1991 | Anderson | 604/385.1 |
| 5,069,678 A | 12/1991 | Yamamoto et al. | 604/385.1 |
| 5,074,854 A | 12/1991 | Davis | 604/385.1 |
| 5,080,741 A | 1/1992 | Nomura et al. | 156/201 |
| 5,087,253 A | 2/1992 | Cooper | 604/385.1 |
| 5,092,861 A | 3/1992 | Nomura et al. | 604/385.2 |
| 5,098,422 A | 3/1992 | Davis et al. | 604/385.1 |
| 5,147,343 A | 9/1992 | Kellenberger | 604/368 |
| 5,147,487 A | 9/1992 | Nomura et al. | 156/164 |
| 5,149,741 A | 9/1992 | Alper et al. | 525/95 |
| D330,590 S | 10/1992 | Pressley et al. | D24/126 |
| 5,158,819 A | 10/1992 | Goodman, Jr. et al. | 428/131 |
| 5,163,932 A | 11/1992 | Nomura et al. | 604/385.2 |
| D331,627 S | 12/1992 | Igaue et al. | D24/124 |
| 5,171,239 A | 12/1992 | Igaue et al. | 604/385.2 |
| 5,171,388 A | 12/1992 | Hoffman et al. | 156/164 |
| 5,188,627 A | 2/1993 | Igaue et al. | 604/385.2 |
| 5,192,606 A | 3/1993 | Proxmire et al. | 428/284 |
| 5,197,960 A | 3/1993 | Nomura et al. | 604/385.2 |
| 5,204,997 A | 4/1993 | Suzuki et al. | 2/400 |
| 5,209,801 A | 5/1993 | Smith | 156/161 |
| 5,234,423 A | 8/1993 | Alemany et al. | 604/385.2 |
| 5,241,710 A | 9/1993 | Lockhart | 2/406 |
| 5,246,433 A | 9/1993 | Hasse et al. | 604/396 |
| 5,275,589 A | 1/1994 | Bozich | 604/373 |
| 5,275,676 A | 1/1994 | Rooyakkers et al. | 156/164 |
| 5,285,531 A | 2/1994 | Nalbandian | 2/406 |
| 5,325,543 A | 7/1994 | Allen | 2/406 |
| 5,342,341 A | 8/1994 | Igaue et al. | 604/385.2 |
| 5,363,511 A | 11/1994 | Brewer | 2/406 |
| 5,368,584 A | 11/1994 | Clear et al. | 604/385.2 |
| 5,370,634 A | 12/1994 | Ando et al. | 604/385.2 |
| 5,382,246 A * | 1/1995 | Kawano | 604/385.2 |
| 5,389,173 A | 2/1995 | Merkatoris et al. | 156/164 |
| 5,413,654 A | 5/1995 | Igaue et al. | 156/161 |
| 5,415,644 A * | 5/1995 | Enloe | 604/385.2 |
| 5,415,649 A | 5/1995 | Watanabe et al. | 604/385.2 |
| 5,440,764 A | 8/1995 | Matsushita | 2/401 |
| 5,449,353 A * | 9/1995 | Watanabe et al. | 604/385.2 |
| 5,486,166 A | 1/1996 | Bishop et al. | 604/366 |
| 5,490,846 A | 2/1996 | Ellis et al. | 604/366 |
| 5,496,429 A | 3/1996 | Hasse et al. | 156/73.3 |
| 5,501,756 A | 3/1996 | Rollins et al. | 156/167 |
| 5,507,895 A | 4/1996 | Suekane | 156/73.1 |
| 5,507,909 A | 4/1996 | Rollins et al. | 156/425 |
| 5,509,915 A | 4/1996 | Hanson et al. | 604/378 |
| 5,540,672 A | 7/1996 | Roessler et al. | 604/385.2 |
| 5,601,544 A | 2/1997 | Glaug et al. | 604/385.2 |
| 5,622,581 A | 4/1997 | Ducker et al. | 156/163 |
| 5,626,574 A | 5/1997 | Sasaki et al. | 604/385.2 |
| 5,626,711 A | 5/1997 | Herrmann | 156/496 |
| 5,634,917 A | 6/1997 | Fujioka et al. | 604/385.2 |
| 5,660,664 A | 8/1997 | Herrmann | 156/161 |
| 5,660,665 A | 8/1997 | Jalonen | 156/163 |
| 5,660,666 A | 8/1997 | Dilnik et al. | 156/259 |
| 5,745,922 A | 5/1998 | Rajala et al. | 2/73 |
| 5,746,731 A | 5/1998 | Hisada | 604/385.2 |
| 5,749,865 A | 5/1998 | Yamamoto et al. | 604/385.2 |
| 5,858,012 A * | 1/1999 | Yamaki et al. | 604/385.2 |
| 5,916,203 A * | 6/1999 | Brandon et al. | 604/367 |
| 6,364,863 B1 | 4/2002 | Yamamoto et al. | |
| 6,478,786 B1 * | 11/2002 | Glaug et al. | 604/385.27 |
| 2002/0072728 A1 * | 6/2002 | Shinohara et al. | 604/385.29 |

DISPOSABLE ABSORBENT UNDERPANTS FOR CONTAINING BODY FLUID

FIELD OF THE INVENTION

This invention relates to disposable absorbent underpants for containing body fluid. More specifically, this invention relates to disposable absorbent underpants for containing at least 100 grams of urine.

BACKGROUND OF THE INVENTION

Disposable underpants have been commercially available for some time for use by infants and toddlers as diapers and training pants. Disposable underpants have also been available for use by adults suffering from incontinence. A number of such underpants have used elastics around the leg openings to form gathers so as to prevent leakage of body fluid from the underpants. When the elastic completely encircles each of the leg openings, it has been found that pressure marks can be left on the thighs of the wearer should the elastic be too tight. It has also been found that when three or more discrete sections of elastics are secured around each leg opening that at the points where the elastics overlap one another, leakage can occur. The overlap of two sections of elastics can also create a bump or hump that can cause irritation and discomfort to the wearer of the underpants.

Now, disposable underpants have been developed which utilize three or more discrete elastic sections that are spaced apart from one another and are positioned about each leg opening. At least two of the discrete elastic sections are separated by a gap. The gap formed between the two adjacent sections assures that the elastics will not overlap one another even when the elastics contract and gather the material to which they are secured. By eliminating such overlaps of the elastics around each leg opening, one can prevent the leakage of body fluid from the underpants.

SUMMARY OF THE INVENTION

Briefly, this invention relates to disposable absorbent underpants for containing body fluid. The disposable underpants include an outer cover having a front portion and a back portion joined together by a crotch portion. An inner liner is attached to the outer cover. The inner liner has at least a front portion and a back portion. The front and back portions of the outer cover and the inner liner-are connected together to form a waist opening and a pair of leg openings. An absorbent pad is secured to the crotch portion. The absorbent pad includes a liquid-permeable cover, a liquid impermeable baffle and an absorbent layer positioned therebetween. A first pair of leg elastics is secured between the outer cover and the inner liner at the front portion such that each of the first pair of leg elastics is positioned adjacent to one of the pair of leg openings. A second pair of leg elastics is secured between the outer cover and the inner liner at the back portion such that each of the second pair of leg elastics is positioned adjacent to one of the pair of leg openings. A third pair of leg elastics is secured to the outer cover. Each of the third pair of leg elastics is a distinct member containing at least one strand of elastic that is at least partially enclosed by a cover sheet. Each of the third pair of leg elastics is positioned adjacent to one of the pair of leg openings intermediate one of the first and second pairs of leg elastics. Each of the third pair of leg elastics is separated from at least one of the first or second pair of leg elastics by a gap. The first, second and third pairs of leg elastics allow gathers to form about each of the leg openings to prevent leakage of body fluid from the underpants. The underpants also contain waist elastic attached between the outer cover and the inner liner at the front and back portions. The waist elastics allow gathers to form about the waist opening to prevent leakage of body fluid from the underpants.

The general object of this invention is to provide disposable absorbent underpants for containing body fluid. A more specific object of this invention is to provide disposable absorbent underpants for containing at least 100 grams of urine.

Another object of this invention is to provide disposable absorbent underpants for an adult suffering from incontinence.

A further object of this invention is to provide disposable absorbent underpants at a reasonable cost that can prevent leakage of body fluid.

Still another object of this invention is to provide disposable absorbent underpants that are easy to manufacture.

Still further, an object of this invention is to provide disposable absorbent underpants that are more comfortable to wear.

Other objects and advantages of the present invention will become more apparent to those skilled in the art in view of the following description and the accompanying drawings.

DETAILED DESCRIPTION OF THE PREFERRED EMBODIMENTS

Figure 1:
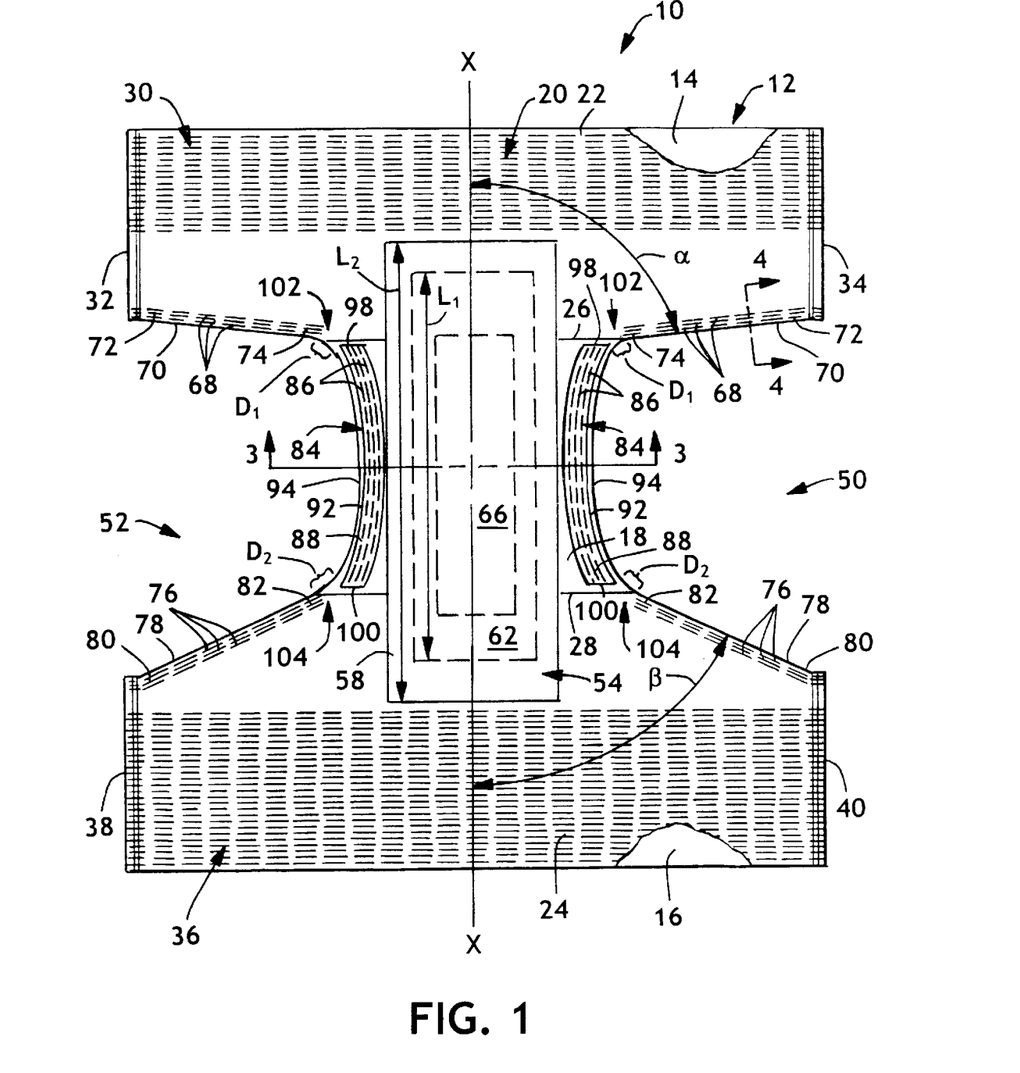
FIG. 1 is a top view of disposable absorbent underpants having two cut-away sections showing an outer cover and an inner liner and having three discrete pairs of leg elastics surrounding each leg opening which are separated from one another by a gap.
Figure 2:
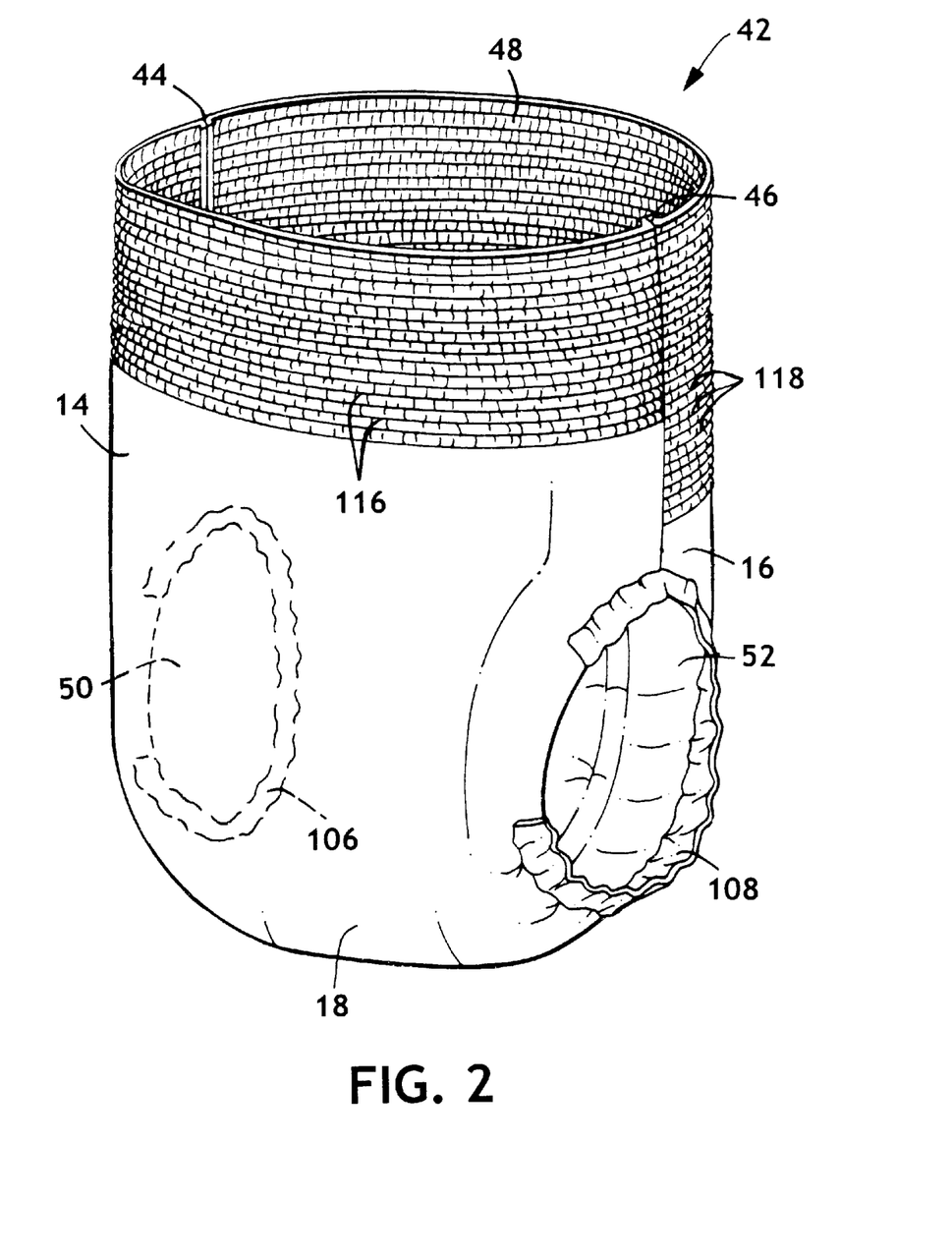
FIG. 2 is a perspective view of the disposable absorbent underpants when the front and back portions are joined together.

Referring to FIG. 1, disposable absorbent underpants 10 are shown in a flat configuration before being formed into a tubular product. The tubular product is depicted in FIG. 2. The underpants 10 are capable of absorbing and containing body fluid, especially urine. The underpants 10 have a longitudinal centerline X—X. The underpants 10 are manufacture and sold as a complete garment. The underpants 10 are designed to be pulled up about the torso of an adult who is suffering from incontinence. However, the underpants 10 could be dimensioned to be a diaper designed to be worn by an infant or be a training pant designed to be worn by a toddler. Preferably, the underpants 10 is an adult incontinent article that can be used day or night to absorb and contain urine.

The disposable underpants 10 is constructed of an outer cover 12 having a front portion 14 and a back portion 16 joined together by a crotch portion 18. The outer cover 12 is located away from the body of the wearer in use. The outer cover 12 can be a single piece of material as shown or it can be made up of two or more separate pieces of material that are joined together. The outer cover 12 should be formed from a soft and flexible material and it can be either liquid-permeable or liquid impermeable. Preferably, the outer cover 12 is liquid impermeable. A suitable material for the outer cover 12 can be made from natural or synthetic fibers and/or films. Examples of natural fibers include cellulose wood fibers and cotton fibers. Examples of synthetic fibers include rayon fibers, polyester fibers, and polypropylene fibers. When a film is utilized, a thermoplastic film formed from a polyolefin, such as polypropylene or polyethylene works well. A combination of natural and synthetic materials can also be used to construct the outer cover 12. The outer cover 12 can also be formed from a woven or a non-woven web. The outer cover 12 can further be formed from a sheet of spunbond, meltblown or a bonded-carded web or from a laminate formed from any of the above-identified materials.

The disposable underpants 10 also contain an inner liner 20. The inner liner 20 is located toward the body of the wearer in use. The inner liner 20 has a front portion 22 and a back portion 24. The front portion 22 has an inner edge 26 and the back portion 24 has an inner edge 28 that are spaced apart from one another. The inner edges 26 and 28 can be located short of the crotch portion 18 or alternatively, can partially extend into the crotch portion 18. The inner liner 20 can be two pieces of material, as shown in FIG. 1, or it can be made up of several pieces of material that are joined together to form the two distinct portions 22 and 24. The inner liner 20 should be formed from a soft and flexible material and it can be either liquid-permeable or liquid impermeable. Preferably, the inner liner 20 is liquid permeable.

The inner liner 20 can be attached or secured to the outer cover 12 by an adhesive, by sewing, by a pressure bond, by a thermal bond, by a pressure and thermal bond, or by another means known to those skilled in the art. The front portion 22 of the inner liner 20 is positioned above or over the front portion 14 of the outer cover 12 while the back portion 24 of the inner liner 20 is positioned above or over the back portion 16 of the outer cover 12. The combination of the-two front portions 14 and 22 create a front waist portion 30 having distally spaced edges 32 and 34. The combination of the back portions 16 and 24 create a back waist portion 36 having distally spaced edges 38 and 40. The edges 32 and 34 of the front waist portion 30 are connected or sealed to the edges, 38 and 40 respectively, of the back waist portion 36 to form a tubular configuration 42, see FIG. 2, adaptable to fit around the torso of a person. The front and back waist portions, 30 and 36 respectively, are secured together to form a pair of side seams or seals 44 and 46. The side seams 44 and 46 can be formed using an ultrasonic bond, by using an adhesive, by using a pressure bond, by using a thermal bond, by using a combination of heat and pressure or by using another means known to those skilled in the art. The tubular configuration 42 has a waist opening 48 and a pair of leg opening 50 and 52. The underpants 10 are designed to fit snugly around the torso of an adult suffering from incontinence and are designed to contain body fluid, especially urine, discharged by the wearer.

Figure 3:
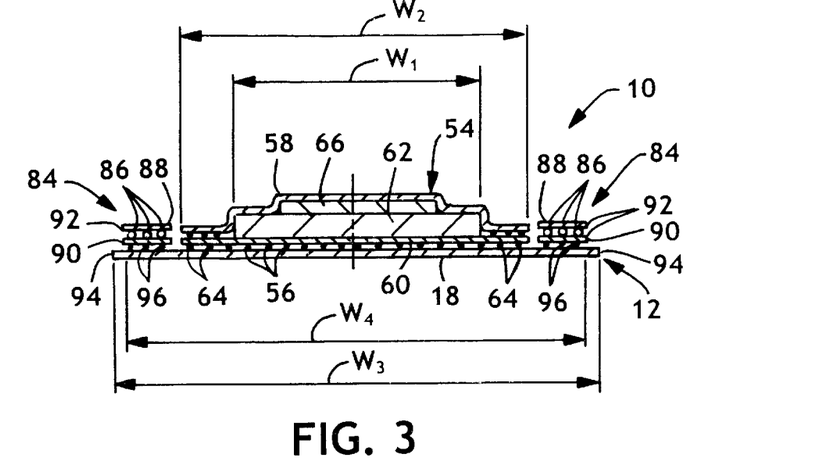
FIG. 3 is a cross-sectional view taken along line 3—3 of FIG. 1 showing the absorbent pad secured to the crotch portion of the inner liner and the third pair of leg elastics as elongated strips secured to the outer cover.

Referring to FIGS. 1–3, an absorbent pad 54 is shown being secured to the crotch portion 18 by an adhesive 56, see FIG. 3. The absorbent pad 54 includes a liquid-permeable cover 58, a liquid impermeable baffle 60 and an absorbent layer 62 positioned therebetween. The liquid-permeable cover 58 and the liquid impermeable baffle 60 are joined or secured together about their peripheries by a construction adhesive 64. The absorbent layer 62 has a length $L_1$, see FIG. 1, and a width $W_1$, see FIG. 3, which are less than the length $L_2$ and the width $W_2$ of the absorbent pad 54. This means that the liquid-permeable cover 58 and the liquid impermeable baffle 60 are larger in size than the absorbent layer 62 and both extend beyond the outer periphery of the absorbent layer 62. This is important because by forming the absorbent layer 62 such that it has a smaller overall size, any body fluid received by the absorbent layer 62 will not be able to flow or wick outward to the outer edges of the absorbent pad 54. This feature will minimize and hopefully prevent the chance of fluid leakage from occurring. The absorbent layer 62 should have a width $W_1$ that is at least about 0.125 inches (about 3.2 mm) less than the width $W_2$ of the absorbent pad 54. Preferably, the absorbent layer 62 will have a width $W_1$ that is from between about 0.25 inches (about 6.4 mm) to about 3 inches (about 76.2 mm) less than the width $W_2$ of the absorbent pad 54. More preferably, the absorbent layer 62 will have a width $W_1$ that is from between about 0.375 inches (about 9.5 mm) to about 1.5 inches (about 38.1 mm) less than the width $W_2$ of the absorbent pad 54.

Referring to FIG. 3, one will notice that the crotch portion 18 of the outer cover 12 has a width $W_3$ and the width $W_2$ of the absorbent pad 54 is less than the width $W_3$ of the crotch portion 18. The absorbent pad 54 should have a width $W_2$ that is at least about 0.125 inches (about 3.2 mm) less than the width $W_3$ of the crotch portion 18. Preferably, the width $W_2$ of the absorbent pad 54 is from between about 0.25 inches (about 6.4 mm) to about 4 inches (about 102 mm) less than the width $W_3$ of the crotch portion 18. More preferably, the absorbent pad 54 will have a width $W_2$ that is from between about 0.375 inches (about 9.5 mm) to about 1.5 inches (about 38.1 mm) less than the width $W_3$ of the crotch portion 18. The reason for this size difference is that the underpants 10 are primarily designed to absorb urine and it is desirable to confine the urine to the absorbent layer 62. The absorbent layer 62 has a width $W_1$ that is less than the width $W_2$ of the absorbent pad 54 and, in turn, the absorbent pad 54 has a width $W_2$ that is less than the width $W_3$ of the crotch portion 18. This size difference assures that if any urine wicks to the longitudinal side edges of the absorbent layer 62 that it will still be spaced apart from the longitudinal side edges of the absorbent pad 54. In turn, the urine will be further away from the longitudinal side edges of the crotch portion 18 and therefore will not leak onto the wearer's clothing or skin.

The liquid-permeable cover 58 can be formed from a liquid-permeable material so as to allow body fluid which strikes the absorbent pad 54 to pass down into the absorbent layer 62. The liquid-permeable cover 58 can be formed from a non-woven web, a spunbond, a meltblown or a bonded-carded web composed of synthetic polymer filaments or fibers. Examples of synthetic materials include polypropylene, polyethylene, polyesters and the like. The liquid-permeable cover 58 can also be formed from a perforated thermoplastic film. Other materials, which can also be utilized to form the cover 58, include rayon and cotton. The liquid-permeable cover 58 can be treated with a surfactant to aid in transfer of the body fluid into the absorbent layer 62, if desired.

The liquid impermeable baffle 60 can be formed from a liquid impermeable material so as to prevent body fluid that contacts it from passing therethrough. The liquid impermeable baffle 60 can be formed from a thin sheet of thermoplastic material such as polyethylene, polypropylene, polyvinyl chloride and the like. Alternatively, the liquid impermeable baffle 60 can be a non-woven, fibrous web that has been constructed to have low liquid permeability. The liquid impermeable baffle 60 can also be constructed from a foam material. In some instances, it may be advantageous to form the liquid impermeable baffle 60 from a material that will allow vapor to pass through but which will prevent body fluid from passing through.

The absorbent layer 62 that is retained between the liquid-permeable cover 58 and the liquid impermeable baffle 60 should be primarily designed to absorb urine. However, it could be constructed to absorb other body fluids, such as menses, blood, perspiration, as well as other body excrements. The absorbent layer 62 can be formed from various natural and/or synthetic materials, such as cellulose fibers, wood pulp fibers, regenerated cellulose or cotton fibers, meltblown fibers, a blend of pulp and other fibers, or a combination of various fibers. A suitable material is "coform" which is a mixture of cellulose fibers and synthetic polymer fibers. Coform is manufactured by Kimberly-Clark Corporation having an office at 401 North Lake Street Neenah, Wis. 54956.

The absorbent layer 62 can also include superabsorbent materials, commonly referred to as "superabsorbents", to increase its absorbency and ability to retain body fluids under pressure loads. The superabsorbents can be present in particle form, as fibers, flakes or in some other structural shape. The superabsorbents can be secured to the absorbent fibers by an adhesive or they can be loosely positioned between the absorbent fibers. Suitable superabsorbents are commercially available from Dow Chemical Company, Hoechst Celanese Corporation and Allied Colloids, Inc.

The absorbent layer 62 may be wrapped in tissue or some similar kind of acquisition and/or distribution layer to assist in maintaining the integrity of the absorbent fibers and the superabsorbents.

It should be noted that the absorbent pad 54 should be designed to absorb at least about 100 grams of body fluid, such as urine. Preferably, the absorbent pad 54 should be designed to absorb from between about 100 grams to about 1500 grams of body fluid. More preferably, the absorbent pad 54 should be designed to absorb about 500 grams of body fluid. Even more preferably, the absorbent pad 54 should be designed to absorb about 1,000 grams of body fluid. Most preferably, the absorbent pad 54 should be designed to absorb about 1,500 grams of body fluid.

A surge layer 66 can optionally be positioned above the absorbent layer 62 such that it is in direct contact with the liquid-permeable cover 58. The purpose of the surge layer 66 is to quickly take up body fluid that contacts the cover 58 and direct this body fluid downward toward the absorbent layer 62. In addition, the surge layer 66 can direct the body fluid outward in the transverse and longitudinal directions so that it is capable of contacting a greater surface area of the absorbent layer 62. This ability to quickly move the body fluid in the x, y and z directions diffuses surges of body fluid which insult the absorbent pad 54. The surge layer 66 is also commonly referred to as an acquisition/distribution layer. The surge layer 66 can be formed from a through-air bonded carded web composed of a blend of 40 percent 6 denier polyester fibers, commercially available from Hoechst Celanese corporation, and 60 percent 3 denier polypropylene/polyethylene sheath core bicomponent fibers, commercially available from Chisso Corporation. The surge layer 66 can have an overall basis weight ranging from about 50 grams per square meter (gsm) to about 120 gsm. In FIG. 1, the surge layer 66 is depicted as having a rectangular configuration but it could be formed into other shapes as well, including an hourglass shape, an oval shape, etc.

Figure 4:
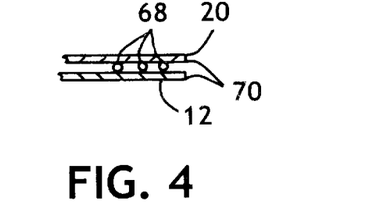
FIG. 4 is a cross-sectional view taken along line 4—4 of FIG. 1 showing one of the first pair of leg elastics sandwiched between the outer cover and the inner liner.

Referring to FIGS. 1 and 4, the underpants 10 includes a first pair of leg elastics 68 secured between the outer cover 12 and the inner liner 20. The first pair of leg elastics 68 is present on the right and left sides of the front waist portion 30. Each of the first pair of leg elastics 68 is positioned adjacent to one of the pair of leg openings, 50 and 52 respectively. The first pair of leg elastics 68 is depicted as being three strands of an elastic material. It should be noted that from 1 to about 12 elastic strands could be utilized if desired. It has been found that three elastic strands provide adequate elastic strength to form gathers about each of the leg openings 50 and 52. The first pair of leg elastics 68 can be secured at intermittent sites to the outer cover 12 and to the inner liner 20 by an adhesive, by ultrasonic bonding, by heat and/or pressure bonds or by some other means known to those skilled in the art. Materials suitable for forming the first pair of leg elastics 68 include polyurethane, rubber, and other elastomeric materials. The first pair of leg elastics 68 can be in the form of long or short elastic strands, elastic tapes, ribbons, yarns, etc. The first pair of leg elastics 68 can have a cross-sectional configuration that is flat, square, rectangular, circular, oval or some other shape. A good material from which the first pair of leg elastics 68 can be formed is LYCRA®. LYCRA® is a registered trademark of the E. I. DuPont de Nemours & Company that has an office at 1002 Market Street, Wilmington, Del. 19801.

Each of the first pair of leg elastics 68 is positioned adjacent to a first pair of edges 70. Each of the first pair of edges 70 is substantially liner in configuration and each extends inward toward the crotch portion 18 from one of the two distally spaced edges 32 and 34. Preferably, at least about 70% of the length of each of the first pair of edges 70 are linear in configuration. Each of the first pair of edges 70 are aligned at an angle alpha ($\alpha$) to the longitudinal centerline X—X of the underpants 10. The angle alpha ($\alpha$) can range from between about 62 degrees to about 99 degrees. Preferably, the angle alpha ($\alpha$) can range from between about 74 degrees to about 91 degrees, and most preferably, the angle alpha ($\alpha$) is at least about 85 degrees. The angling of the first pair of edges 70 relative to the longitudinal centerline X—X ensures a better contouring of the underpants 10 to the body and provides a comfortable fit with reduced bunching.

The first pair of leg elastics 68 are located along and are preferably aligned parallel to the first pair of edges 70. Each of the first pair of leg elastics 68 has a first end 72 located adjacent to or coterminous to one of the distal edges, 32 and 34 respectively. Preferably, each of the first ends 72 is spaced slightly inward from one of the two distal edges 32 and 34. The first pair of leg elastics 68 should extend toward the absorbent pad 54 but should stop short thereof. Each of the first pair of leg elastics 68 terminates at a second end 74. Each second end 74 is located away from the outer periphery of the absorbent pad 54. The exact distance of the second ends 74 from the outer periphery of the absorbent pad 54 can vary from between about 1 millimeter to about 100 millimeters, and preferably, the distance is less than about 50 millimeters.

The underpants 10 also include a second pair of leg elastics 76 secured between the outer cover 12 and the inner liner 20. The second pair of leg elastics 76 is present on the right and left sides of the back waist portions 36. Each of the second pair of leg elastics 76 is positioned adjacent to one of the pair of leg openings, 50 and 52 respectively. The second pair of leg elastics 76 is depicted as being three strands of an elastic material. It should be noted that from 1 to about 12 elastic strands could be utilized if desired. It has been found that three strands provide adequate elastic strength to form gathers about each of the leg openings 50 and 52. The second pair of leg elastics 76 can be secured at intermittent sites to the outer cover 12 and to the inner liner 20 by an adhesive, by ultrasonic bonding, by heat and/or pressure bonds or by some other means known to those skilled in the art. Materials suitable for forming the second pair of elastics 76 include those described above with reference to the first pair of leg elastics 68. Like the first pair of elastics 68, the second pair of leg elastics 76 can be in the form of long or short elastic strands, elastic tapes, ribbons, yarns, etc. The second pair of leg elastics 76 can have a cross-sectional configuration that is flat, square, rectangular, circular, oval or some other shape.

Each of the second pair of leg elastics 76 is positioned adjacent to a second pair of edges 78. Each of the second pair of edges 78 is substantially liner in configuration and extends inward toward the crotch portion 18 from the two distally spaced edges 38 and 40. Preferably, at least about 70% of the length of each of the second pair of edges 78 are linear in configuration. Each of the second pair of edges 78 are aligned at an angle beta (β) to the longitudinal centerline X—X of the underpants 10. The angle beta (β) can range from between about 45 degrees to about 89 degrees. Preferably, the angle beta (β) can range from between about 55 degrees to about 87 degrees, and most preferably, the angle beta (β) is from between about 61 degrees to about 76 degrees. The angling of the second pair of edges 78 relative to the longitudinal centerline X—X ensures a better contouring of the underpants 10 to the body and provides a comfortable fit with reduced bunching.

The second pair of leg elastics 76 are located along and are preferably aligned parallel to the second pair of edges 78. Each of the second pair of leg elastics 76 has a first end 80 located adjacent to or coterminous to one of the distal edges, 38 and 40 respectively. Preferably, each of the first ends 80 is spaced slightly inward from one of the two edges 38 and 40. The second pair of leg elastics 76 should extend toward the absorbent pad 54 but should stop short thereof. Each of the second pair of leg elastics 76 terminates at a second end 82. Each second end 82 is located away from the outer periphery of the absorbent pad 54. The exact distance can vary from between about 1 millimeter to about 100 millimeters, and preferably, the distance is less than about 50 millimeters.

Referring to FIGS. 1 and 3, the disposable absorbent underpants 10 further include a third pair of leg elastics 84. Each of the third pair of leg elastics 84 is an elongated strip present on the right and left sides of the crotch portion 18. Each of the third pair of leg elastics 84 is positioned adjacent to one of the leg openings 50 and 52 intermediate one of the first and second pairs of leg elastics, 68 and 76 respectively. Each of the third pair of leg elastics 84 is a distinct member secured to the outer cover 12. Each of the third pair of leg elastics 84 contains at least one strand of elastic material 86 that is at least partially enclosed by a pair of carrier sheets 88 and 90. Preferably, there are at least two and, more preferably, at least three strands of elastic material 86 that are completely enclosed by the pair of carrier sheets 88 and 90. Each of the carrier sheets 88 and 90 has an arcuately configured edge 92 that closely matches or resembles the arcuate profile or curvature of a third pair of edges 94 present in the crotch portion 18. Each arcuate edge 92 is shown positioned slightly inward from one of the arcuately shaped, third pair of edges 94. The exact distance that each of the arcuate edges 92 are positioned and secured inward of one of the third pair of edges 94 can vary. The distance each of the arcuate edges 92 are secured inward from one of the third pair of edges 94 should be from between about 0.1 inches to about 0.8 inches (about 2.5 mm to about 20.3 mm). Preferably, the distance each of the arcuate edges 92 are secured inward from one of the third pair of edges 94 will be from between about 0.15 inches to about 0.5 inches (about 3.8 mm to about 12.7 mm). More preferably, each of the arcuate edges 92 is secured inward about 0.5 inches (about 12.7 mm) from one of the third pair of edges 94. Most preferably, each of the arcuate edges 92 is secured inward about 0.25 inches (about 6.4 mm) from one of the third pair of edges 94.

If desired, the arcuate edges 92 of the carrier sheets 88 and 90 can be aligned coterminous to the third pair of edges 94.

It should be noted that each of the third pair of leg elastics 84 can include one or more strands of an elastic material 86. It has been found that three strands provide adequate elastic strength to form gathers about each of the leg openings 50 and 52.

The lower carrier sheet 90 can be secured continuously or at intermittent sites to the outer cover 12 by an adhesive 96. Other forms of attachment can also be used including ultrasonic bonding, heat and/or pressure bonds or by some other means known to those skilled in the art. Materials suitable for forming the third pair of leg elastics 84 include those described above with reference to the first and second pairs of leg elastics, 68 and 76 respectively. Like the first and second pairs of leg elastics, 68 and 76 respectively, the third pair of leg elastics 84 can be in the form of long or short elastic strands, elastic tapes, ribbons, yarns, etc. The third pair of leg elastics 84 can have a cross-sectional configuration that is flat, square, rectangular, circular, oval or some other shape.

As stated above, each of the third pair of leg elastics 84 is an elongated strip positioned adjacent to and preferably is aligned parallel to the third pair of edges 94. The third pair of edges 94 forms the outside periphery of the crotch portion 18. Each of the third pair of edges 94 has an arcuate or curved configuration and the two side edges 94 are distally spaced from one another. Each of the third pair of leg elastics 84 is positioned intermediate one of the first and second pairs of leg elastics 68 and 76 respectively. Each of the third pair of leg elastics 84 has a first end 98 and a second end 100. The first end 98 of each of the third pair of leg elastics 84 is separated from the second end 74 of the first pair of leg elastics 68 by a first pair of gaps 102. One of the first pair of gaps 102 is located on the right side of the underpants 10 adjacent to the leg opening 50. The second of the first pair of gaps 102 is located on the left side of the underpants 10 adjacent to the leg opening 52. The dimension of each of the first pair of gaps 102 is denoted as "$D_1$" and $D_1$ can be at least about 0.125 inches (about 3.2 mm) in length. Preferably, the dimension $D_1$ of each of the first pair of gaps 102 is from between about 0.25 inches (about 6.4 mm) to about 9 inches (about 229 mm). More preferably, the dimension $D_1$ of each of the first pair of gaps 102 is from between about 0.375 inches (about 9.5 mm) to about 5 inches (about 127 mm). Most preferably, the dimension $D_1$ of each of the first pair of gaps 102 is from between about 0.5 inches (about 12.7 mm) to about 2 inches (about 51 mm). The dimension $D_1$ is measured when the underpants 10 are in a flat, extended orientation similar to that depicted in FIG. 1.

Likewise, the second end 100 of each of the third pair of leg elastics 84 is separated from the second end 82 of the second pair of leg elastics 76 by a distance "$D_2$" by a second pair of gaps 104. One of the second pair of gaps 104 is located on the right side of the underpants 10 adjacent to the leg opening 50. The other of the second pair of gaps 104 is located on the left side of the underpants 10 adjacent to the leg opening 52. The dimension of each of the second pair of gaps 104 is denoted as "$D_2$" and $D_2$ can be at least about 0.125 inches (about 3.2 mm) in length. Preferably, the dimension $D_2$ of each of the second pair of gaps 104 is from between about 0.25 inches (about 6.4 mm) to about 9 inches (about 229 mm). More preferably, the dimension $D_2$ of each of the second pair of gaps 104 is from between about 0.375 inches (about 9.5 mm) to about 5 inches (about 127 mm). Most preferably, the dimension $D_2$ of each of the second pair of gaps 104 is from between about 0.5 inches (about 12.7 mm) to about 2 inches (about 51 mm). The dimension $D_2$ is measured when the underpants 10 are in a flat, extended orientation similar to that depicted in FIG. 1. To measure the distance of the gap $D_2$, one should mark the gathered ends 82 and 100 of the second and third pairs of leg elastics 76 and 84 in a relaxed state. The underpants 10 are then extended until all the material is flat, as depicted in FIG. 1. In this configuration, the two pair of leg elastics 76 and 84 will be stretched out and the actual distance between the marks will represent the dimension of the gap $D_2$.

It should be noted that two pairs of gaps 102 and 104 have been described. However, if one desired to use only one of the two pairs of gaps, 102 and 104, that this can be done. One could also use additional gaps, if desired, without destroying the function of this invention. It is also possible to form a single gap 102 on one side of the longitudinal centerline X—X and to form a single gap 104 on the opposite side of the longitudinal centerline X—X. However, preferably, the two pairs of gaps 102 and 104 will be utilized.

Referring again to FIG. 2, gathers 106 and 108 are formed around the first and second leg openings, 50 and 52 respectively as the first, second and third leg elastics 68, 76 and 84 contract. The first and second pairs of gaps, 102 and 104 respectively, cooperate with the first, second and third pairs of leg elastics, 68, 76 and 84 to form the gathers 106 and 108. The gathers 106 and 108 will form a snug fit around the entire circumference of each of the leg openings 50 and 52. The two pairs of gaps 102 and 104 will prevent the adjacent first, second and third pairs of leg elastics 68, 76 and 84 from overlapping one another and forming bumps and/or humps around the leg openings 50 and 52. By eliminating such bumps and humps, one can prevent the leakage of body fluid through the leg openings 50 and 52. It is very important that fluid leakage from around the leg openings 50 and 52 be eliminated because if such leakage occurs, the usefulness of the underpants 10 is compromised.

Even though the two pairs of gaps 102 and 104 are present in the stretched out, flat orientation shown in FIG. 1, the contraction force of the first, second and third pairs of leg elastics 68, 76 and 84 will cause the gathers 106 and 108 to form. The force of the first, second and third pairs of leg elastics 68, 76 and 84 positioned adjacent to the gaps 102 and 104 will cause the material forming the outer cover 12 and the inner liner 20 to fit snug against the thighs of the wearer during use. No fluid channels will occur at the locations of the first and second pairs of gaps 102 and 104. This will assure that no body fluid will be able to leak out through these locations ($D_1$ and $D_2$) during normal use.

Figure 5:
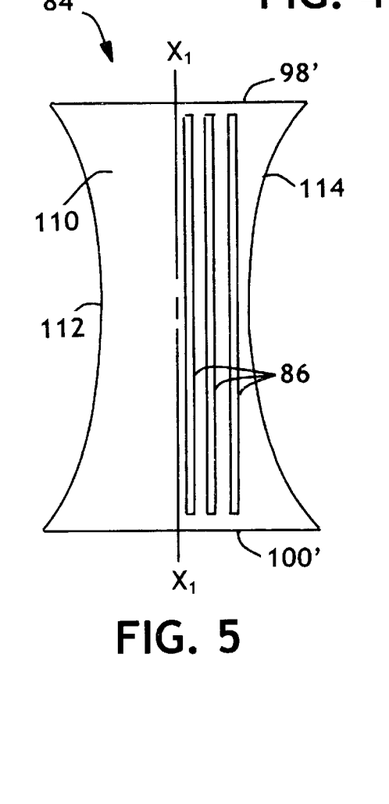
FIG. 5 is a top view of three elastic strands aligned to one side of the longitudinal central axis of an hourglass shaped carrier sheet.
Figure 6:
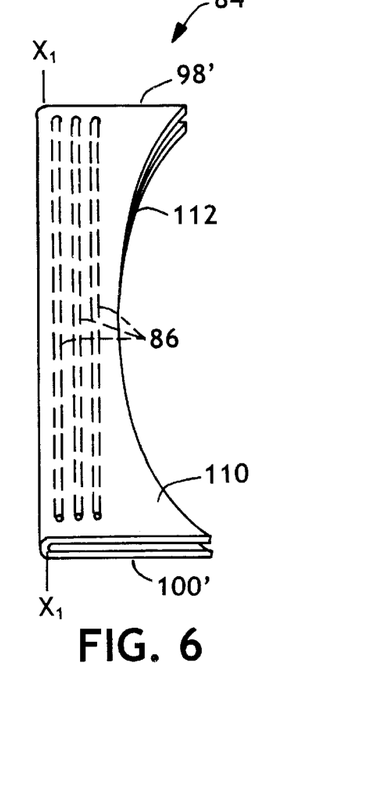
FIG. 6 is a perspective view of the carrier sheet shown in FIG. 5 folded along its longitudinal central axis.

Referring now to FIGS. 5 and 6, an alternative embodiment is depicted for forming a third pair of leg elastic 84'. Each of the third pair of leg elastic 84' has an hourglass shaped carrier sheet 110. The carrier sheet 110 is preferably an elongated member having a longitudinal central axis $X_1$—$X_1$ and a pair of distally spaced arcuate sides 112 and 114. Three or more strands of elastic 86 can be aligning or positioning on the hourglass shaped carrier sheet 110. Preferably, the elastic strands 86 are located to one side of the longitudinal central axis $X_1$—$X_1$. The hourglass shaped carrier sheet 110 can then be folded along its longitudinal central axis $X_1$—$X_1$, as shown in FIG. 6, to a third leg elastic 84'. When the carrier sheet 110 is folded, the arcuate side 112 will overlap the arcuate side 114 and form an arcuate edge that matches the curvature of each of the third edges 94 of the crotch portion 18.

Figure 7:
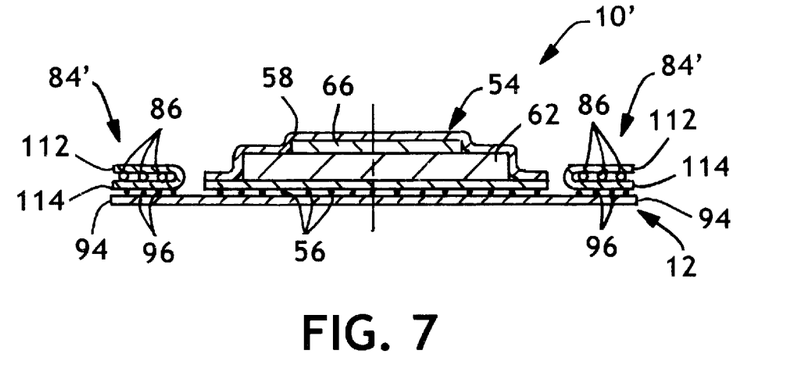
FIG. 7 is a cross-sectional view of an alternative embodiment taken through the crotch portion showing the third pair of leg elastics folded into elongated strips having an outer edge coterminously aligned with the outer side edge of the outer cover.

Referring to FIG. 7, a cross-sectional view of the crotch portion of disposable underpants 10' is depicted which is similar to FIG. 3 except for the substitution and location of the third pair of leg elastics 84'. Each of the third pair of leg elastic 84', shown in FIG. 6, is an elongated strip which is positioned on the outer cover 12. One of the third pair of leg elastic 84' is secured to the outer cover 12 on the left side of the absorbent pad 54 and the other of the third pair of leg elastic 84' is secured to the outer cover 12 on the right side of the absorbent pad 54. In this embodiment, the arcuate edges 112 and 114 of the third pair of leg elastic 84' are aligned coterminous to the third pair of edges 94. If desired, the arcuate edges 112 and 114 can be aligned slightly inward of the third pair of edges 94.

Figure 8:
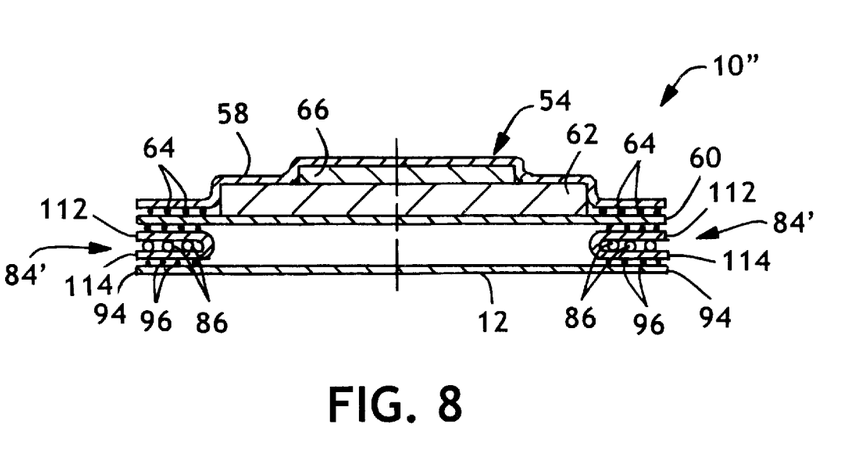
FIG. 8 is a cross-sectional view of another alternative embodiment taken through the crotch portion showing the third pair of leg elastics folded into elongated strips and secured to a lower surface of the absorbent pad.

Referring to FIG. 8, a cross-sectional view of the crotch portion of still another embodiment of disposable underpants 10'' is depicted. In this embodiment, the third pair of leg elastic 84' is secured between the lower surface of the liquid impermeable baffle 60 and the upper surface of the outer cover 12. Again, the arcuate edges 112 and 114 the third pair of leg elastic 84' are aligned coterminous to the third pair of edges 94 of the crotch portion 18. If desired, the arcuate edges 112 and 114 can be aligned slightly inward of the third pair of edges 94. One will notice that in this embodiment, the liquid impermeable baffle 60 is not adhesively attached to the outer cover 12. However, adhesive could be used to attach the liquid impermeable baffle 60 to the outer cover 12, if desired.

Referring again to FIGS. 1 and 2, the disposable absorbent underpants 10 further has waist elastic 116 attached to the front waist portion 30 and waist elastic 118 attached to the back waist portion 36. The waist elastics 116 and 118 can include threads, strands, ribbons, bands, film, elastic nonwovens or composites. The threads, strands, ribbons, etc. may be a multitude of singular members or they may be applied as a composite. The number of elastic members can range from 1 to over a 100. Preferably, the number of elastic members will range from between about 10 to about 40, and most preferably, from about 15 to about 35. There can be an equal number or a different number of waist elastics 116 in the front waist portion 30 versus the number of waist elastics 118 in the back waist portion 36. The waist elastics 116 and 118 can be individual threads that are spaced apart from one another from between about 0.063 inches (about 1.6 mm) to about 2.0 inches (about 51 mm). Preferably, the waist elastics 116 and 118 can be individual threads that are spaced apart from one another by about 0.25 inches (about 6.4 mm). While the appearance of the underpants 10 may be enhanced by the close even spacing of the waist elastics 116 and 118, the exact distance between adjacent waist elastics 116 or 118 can vary.

The waist elastics 116 and 118 may be made from any suitable elastomeric material. One suitable material is LYCRA®. LYCRA® is a registered trademark of the E. I. DuPont de Nemours & Company that has an office at 1002 Market Street, Wilmington, Del. 19801. Suitable waist elastics 116 and 118 include threads having a decitex (grams/10,000 meters) of from between about 100 to about 1,200, preferably, from between about 470 to about 940, and most preferably, from between about 620 to about 740. The waist elastics 116 and 118 can be secured to the outer cover 12 and/or to the inner liner 20 by a hot or cold melt adhesive applied in a variety of spray patterns. One spray pattern that has been used with good success is a swirl pattern. A preferred adhesive is a hot melt adhesive sold as Findley H2096 by ATO Findley Adhesives having an office in Milwaukee, Wis.

The waist elastics 116 and 118 allow gathers (not shown) to form about the waist opening 48 to prevent leakage of body fluid from the underpants 10. The number of gathers formed will depend on the number of elastic strands present, the spacing between each elastic strand, the contraction force of the elastic strands, the material from which the outer cover 12 and the inner liner 20 are constructed, as well as other factors.

While the invention has been described in conjunction with several specific embodiments, it is to be understood that many alternatives, modifications and variations will be apparent to those skilled in the art in light of the aforegoing description. Accordingly, this invention is intended to embrace all such alternatives, modifications and variations that fall within the spirit and scope of the appended claims.

We claim:

1. A disposable absorbent underpants for containing body fluid comprising:
   a) an outer cover having a front portion and a back portion joined together by a crotch portion;
   b) an inner liner attached to said outer cover, said inner liner having at least a front portion and a back portion,, said front and back portions of said outer cover and said inner liner being connected together to form a waist opening and a pair of leg openings;
   c) an absorbent pad positioned over said crotch portion, said absorbent pad including a liquid-permeable cover, a liquid impermeable baffle, and an absorbent layer positioned therebetween;
   d) a first pair of leg elastics secured between said front portion of said outer cover and said inner liner, each of said first pair of leg elastics being positioned adjacent to one of said pair of leg openings;
   e) a second pair of leg elastics secured between said back portion of said outer cover and said inner liner, each of said second pair of leg elastics being positioned adjacent to one of said pair of leg openings;
   f) a third pair of leg elastics secured to said outer cover, each of said third pair of leg elastics being a distinct member containing at least one strand of elastic that is at least partially enclosed by a carrier sheet, each of said third pair of leg elastics being positioned adjacent to one of said leg openings intermediate one of said first and second pairs of leg elastics, each of said third pair of leg elastics being separated from one of said first pair of leg elastics by a first gap and from said second pair of leg elastics by a second gap, said first, second and third pairs of leg elastics allowing gathers to form about each of said leg openings to prevent leakage of body fluid from said underpants; and
   g) waist elastic attached to said front and back portions between said outer cover and said inner liner, said waist elastics allowing gathers to form about said waist opening to prevent leakage of body fluid from said underpants.

2. The disposable absorbent underpants of claim 1 wherein said carrier sheet includes two distinct sheets and at least three strands of elastics are secured between said two distinct sheets.

3. The disposable absorbent underpants of claim 2 wherein said at least three strands of elastics are secured to said two carrier sheets by an adhesive.

4. The disposable absorbent underpants of claim 1 wherein said crotch portion includes a pair of edges having an arcuate shape and each of said third pair of leg elastics is secured within 0.25 inches from one of said pair of edges of said crotch portion.

5. The disposable absorbent underpants of claim 4 wherein each of said third pair of leg elastics is an elongated strip having an arcuate configuration matching one of said pair of edges of said crotch portion.

6. The disposable absorbent underpants of claim 1 wherein each of said third pair of leg elastics is an elongated strip having an outer edge coterminously aligned with one of said pair of edges of said crotch portion.

7. The disposable absorbent underpants of claim 1 wherein each of said third pair of leg elastics is an elongated strip having an outer edge spaced inward from one of said pair of edges of said crotch portion.

8. The disposable absorbent underpants of claim 7 wherein said outer edge of each of said third pair of leg elastics is spaced inward a distance of from between about 0.1 inches to about 0.8 inches from one of said pair of edges of said crotch portion.

9. The disposable absorbent underpants of claim 8 wherein said outer edge of each of said third pair of leg elastics is spaced inward a distance of from between about 0.15 inches to about 0.5 inches from one of said pair of edges of said crotch portion.

10. A disposable absorbent underpants for containing body fluid comprising:
    a) an outer cover having a front portion and a back portion joined together by a crotch portion;
    b) an inner liner attached to said outer cover, said inner liner having at least a front portion and a back portion, said front and back portions of said outer cover and said inner liner being connected together to form a waist opening and a pair of leg openings;
    c) an absorbent pad positioned over said crotch portion, said absorbent pad including a liquid-permeable cover, a liquid impermeable baffle, and an absorbent layer positioned therebetween, said absorbent pad having a capacity for absorbing about 100 grams of body fluid;
    d) a first pair of leg elastics secured between said front portion of said outer cover and said inner liner, each of said first pair of leg elastics being positioned adjacent to one of said pair of leg openings;
    e) a second pair of leg elastics secured between said back portion of said outer cover and said inner liner, each of said second pair of leg elastics being positioned adjacent to one of said pair of leg openings;
    f) a third pair of leg elastics secured to said outer cover, each of said third pair of leg elastics being a distinct member containing at least one strand of elastic that is at least partially enclosed by a carrier sheet, each of said third pair of leg elastics being positioned adjacent to one of said leg openings intermediate one of said first and second pairs of leg elastics, each of said third pair of leg elastics being separated from one of said first pair of leg elastics by a first gap and from said second pair of leg elastics by a second gap, each of said first and second gaps being at least 0.25 inches in length, said first, second and third pairs of leg elastics allowing gathers to form about each of said leg openings to prevent leakage of body fluid from said underpants; and g) waist elastic attached to said front and back portions between said outer cover and said inner liner, said waist elastics allowing gathers to form about said waist opening to prevent leakage of body fluid from said underpants.

11. The disposable absorbent underpants of claim 10 wherein said carrier sheet is an elongated member having an hourglass shape.

12. The disposable absorbent underpants of claim 11 wherein said carrier sheet has a longitudinal central axis and at least three strands of elastics are positioned to one side of said longitudinal central axis, and said carrier sheet is folded upon itself along said longitudinal central axis to form an elongated strip.

13. The disposable absorbent underpants of claim 10 wherein said crotch portion has a pair of edges and each of said third pair of leg elastics has an outer edge coterminously aligned with one of said pair of edges.

14. The disposable absorbent underpants of claim 13 wherein each of said third pair of leg elastics has an outer edge spaced inward from one of said pair of edges of said crotch portion.

15. A disposable absorbent underpants for containing body fluid comprising:

a) an outer cover having a front portion and a back portion joined together by a crotch portion;

b) an inner liner attached to said outer cover, said inner liner having at least a front portion and a back portion, said front and back portions of said outer cover and said inner liner being connected together to form a waist opening and a pair of leg openings;

c) an absorbent pad positioned over said crotch portion, said absorbent pad including a liquid-permeable cover, a liquid impermeable baffle, and an absorbent layer positioned therebetween, said absorbent pad having a capacity for absorbing about 500 grams of body fluid;

d) a first pair of leg elastics secured between said front portion of said outer cover and said inner liner, each of said first pair of leg elastics being positioned adjacent to one of said pair of leg openings;

e) a second pair of leg elastics secured between said back portion of said outer cover and said inner liner, each of said second pair of leg elastics being positioned adjacent to one of said pair of leg openings;

f) a third pair of leg elastics secured to said outer cover, each of said third pair of leg elastics being a distinct member containing at least three strands of elastics that are secured between a cover sheet and a backing sheet, each of said third pair of leg elastics being positioned adjacent to one of said leg openings intermediate one of said first and second pairs of leg elastics, each of said third pair of leg elastics being separated from one of said first pair of leg elastics by a first gap and from said second pair of leg elastics by a second gap, each of said first and second gaps being at least 0.5 inches in length, said first, second and third pairs of leg elastics allowing gathers to form about each of said leg openings to prevent leakage of body fluid from said underpants; and g) waist elastic attached to said front and back portions between said outer cover and said inner liner, said waist elastics allowing gathers to form about said waist opening to prevent leakage of body fluid from said underpants.

16. The disposable absorbent underpants of claim 15 wherein said crotch portion includes a pair of edges, said pair of edges being distally spaced from one another and having an arcuate shape.

17. The disposable absorbent underpants of claim 16 wherein each of said third pair of leg elastics is in the form of an elongated strip having an outer edge coterminously aligned with one of said pair of edges.

18. The disposable absorbent underpants of claim 16 wherein each of said third pair of leg elastics is in the form of an elongated strip having an outer edge spaced inward from one of said pair of edges.

19. The disposable absorbent underpants of claim 18 wherein each of said third pair of leg elastics is secured within 0.25 inches from one of said pair of edges.

20. The disposable absorbent underpants of claim 18 wherein each of said third pair of leg elastics is secured within 0.5 inches from one of said pair of edges.

21. A disposable absorbent underpants for containing body fluid comprising:

a) an outer cover having a front portion and a back portion joined together by a crotch portion;

b) an inner liner attached to said outer cover, said inner liner having at least a front portion and a back portion, said front and back portions of said outer cover and said inner liner being connected together to form a waist opening and a pair of leg openings;

c) an absorbent pad positioned over said crotch portion, said absorbent pad including a liquid-permeable cover, a liquid impermeable baffle, and an absorbent layer positioned therebetween;

d) a first pair of leg elastics secured between said front portion of said outer cover and said inner liner, each of said first pair of leg elastics being positioned adjacent to one of said pair of leg openings;

e) a second pair of leg elastics secured between said back portion of said outer cover and said inner liner, each of said second pair of leg elastics being positioned adjacent to one of said pair of leg openings;

f) a third pair of leg elastics secured to said outer cover, each of said third pair of leg elastics being a distinct member containing at least one strand of elastic that is at least partially enclosed by a carrier sheet, each of said third pair of leg elastics being positioned adjacent to one of said leg openings intermediate one of said first and second pairs of leg elastics, each of said third pair of leg elastics being separated from at least one of said first or said second pair of leg elastics by a gap, said first, second and third pairs of leg elastics allowing gathers to form about each of said leg openings to prevent leakage of body fluid from said underpants; and g) waist elastic attached to said front and back portions between said outer cover and said inner liner, said waist elastics allowing gathers to form about said waist opening to prevent leakage of body fluid from said underpants.

22. The absorbent article of claim 21 wherein the absorbent pad has a width $W_2$, and $W_2$ is sized such that the absorbent pad does not overlap the third pair of leg elastics.

23. The absorbent article of claim 22 wherein each of said third pair of leg elastics is separated from said first pair of leg elastics by a first gap and separated from said second pair of leg elastics by a second gap, and said first and second gaps are at least about 0.125 inches in length.

* * * * *